United States Patent
Arayama et al.

(10) Patent No.: US 9,433,541 B2
(45) Date of Patent: Sep. 6, 2016

(54) DISPOSABLE WEARING ARTICLE

(75) Inventors: Takaya Arayama, Kagawa (JP); Hirotomo Mukai, Kagawa (JP)

(73) Assignee: UNICHARM CORPORATION, Ehime-Ken (JP)

(*) Notice: Subject to any disclaimer, the term of this patent is extended or adjusted under 35 U.S.C. 154(b) by 394 days.

(21) Appl. No.: 13/984,795

(22) PCT Filed: Feb. 9, 2012

(86) PCT No.: PCT/JP2012/000888
§ 371 (c)(1),
(2), (4) Date: Oct. 16, 2013

(87) PCT Pub. No.: WO2012/108206
PCT Pub. Date: Aug. 16, 2012

(65) Prior Publication Data
US 2014/0031783 A1   Jan. 30, 2014

(30) Foreign Application Priority Data
Feb. 10, 2011   (JP) .................... 2011-027618

(51) Int. Cl.
*A61F 13/15* (2006.01)
*A61F 13/53* (2006.01)
(Continued)

(52) U.S. Cl.
CPC ......... *A61F 13/53* (2013.01); *A61F 13/49001* (2013.01); *A61F 13/49413* (2013.01); *A61F 13/53409* (2013.01); *A61F 13/49007* (2013.01); *A61F 13/49017* (2013.01); *A61F 13/49019* (2013.01)

(58) Field of Classification Search
CPC .............. A61F 13/49017; A61F 13/49019; A61F 13/49001; A61F 13/49007

USPC .......... 604/385.101, 385.11, 385.16, 385.22, 604/385.28, 385.27, 385.24, 385.31, 385.17
See application file for complete search history.

(56) References Cited

U.S. PATENT DOCUMENTS

2006/0069371 A1   3/2006   Ohashi et al.
2006/0264859 A1*  11/2006  Tsuji ................. A61F 13/49012
                                                         604/385.28
2012/0143162 A1   6/2012   Mukai et al.

FOREIGN PATENT DOCUMENTS

EP   2520262 A1   11/2012
EP   2684546 A1   1/2014
(Continued)

OTHER PUBLICATIONS

International Search Report and Written Opinion corresponding to PCT/JP2012/000888, dated May 15, 2012.
(Continued)

Primary Examiner — Jacqueline Stephens
(74) Attorney, Agent, or Firm — Hauptman Ham, LLP

(57) ABSTRACT

A disposable wearing article includes a central curving unit that allows the absorber to curve in the inner direction in a convex shape is formed in the center of the absorber, a pair of first curving units along the front-back direction that allow the absorber to curve in the outer direction in a convex shape is formed outboard of the central curving unit of the absorber, a pair of second curving units along the front-back direction that allow the absorber to curve in the inner direction in a convex shape is formed outboard of the first curving unit of the absorber, and a front end of the central curving unit is positioned posteriorly of a front end of a second curving unit.

14 Claims, 10 Drawing Sheets

(51) Int. Cl.
*A61F 13/494* (2006.01)
*A61F 13/534* (2006.01)
*A61F 13/49* (2006.01)

(56) References Cited

FOREIGN PATENT DOCUMENTS

| | | |
|---|---|---|
| JP | 2005-034652 A | 2/2005 |
| JP | 2006-095156 A | 4/2006 |
| JP | 2006-122396 A | 5/2006 |
| JP | 2007-144105 A | 6/2007 |
| JP | 2010-042162 A | 2/2010 |
| JP | 2010-279612 A | 12/2010 |
| WO | 2011/105109 A1 | 9/2011 |

OTHER PUBLICATIONS

Extended European Search Report issued Feb. 20, 2015, corresponding to European patent application No. 12744332.3.
Office Action mailed Aug. 4, 2014, corresponding to Chinese patent application No. 201280008284.8.

* cited by examiner

US 9,433,541 B2

DISPOSABLE WEARING ARTICLE

RELATED APPLICATIONS

The present application is a National Phase of International Application Number PCT/JP2012/000888, filed Feb. 9, 2012, and claims priority from Japanese Application Number 2011-027618, filed Feb. 10, 2011.

TECHNICAL FIELD

The present disclosure relates to a disposable wearing article.

BACKGROUND ART

In a disposable wearing article, such as a pants-type diaper, to improve the comfort of the wearer when worn and to prevent the leakage of excretions, various methods have been devised. For example, a pants-type diaper in which five curving units are formed along the front-back direction of the absorber in an absorber that absorbs the excretions of the wearer is known, (for example, PTL 1).

More specifically, in the pants-type diaper, five slits are formed in the absorber, and when worn, each slit's peripheral portion curves, respectively. The central slit's peripheral portion forms a convex shape facing the excretory opening of the wearer. Furthermore, each intermediate slit's peripheral portion positioned outboard of the central slit in the widthwise direction forms a convex shape at the reverse side of the central slit's peripheral portion, that is, a concave shape with respect to the excretory opening. Furthermore, each side slit's peripheral portion positioned outboard of the intermediate slits forms a convex shape facing the excretory opening of the wearer.

That is, convex-shaped portions and concave-shaped portions are formed with mutual adjacency along the widthwise direction in the absorber. Because the central portion of the absorber is in contact with the crotch portion of the wearer, the absorption performance can be improved. Furthermore, because the absorber curves along the crotch portion due to a plurality of convex-shaped portions and concave-shaped portions, the fitting improves.

CITATION LIST

Patent Literature

PTL 1: Japanese Unexamined Patent Application Publication No. 2005-34652 (page 12, FIG. 5)

SUMMARY OF INVENTION

Technical Problem

However, the inventor(s) has/have recognized that, in the above-described pants-type diaper, the length of the center slit in the lengthwise direction and the length of the side slit in the lengthwise direction are almost equal. Thus, the length of the convex-shaped portion positioned in the center of the absorber and the length of the convex-shaped portion positioned at the side of the absorber are almost equal. However, the shape at the center of the crotch portion of the wearer and the shape at the side of the crotch portion are different. Thus, the wearing comfort might get deteriorated due to the occurrence of a gap between the body of the wearer and the absorber, and also due to excessive adhesion.

Thus, the purpose of the present invention is to provide a disposable wearing article, such as a pant-type diaper that can alleviate the deterioration in the comfort when worn in cases where the absorption performance is increased by curving the absorber in a convex shape.

Solution to Problem

A disposable wearing article includes an absorber having a front-back direction, a widthwise direction perpendicular to the front-back direction, an inner direction for facing the wearer, and an outer direction opposite the inner direction.

The absorber has a central portion formed in the center of the absorber in the widthwise direction, a pair of side end portions including side ends of the absorber in the widthwise direction, and a pair of intermediate portions positioned between the central portion and the side end portions, in a crotch region that is adapted to be in contact with a crotch of the wearer. A central curving unit that allows the absorber to curve in the inner direction in a convex shape is formed in the center of the absorber. A pair of first curving units along the front-back direction that allow the absorber to curve in the outer direction in a convex shape is formed outboard of the central curving unit of the absorber in the widthwise direction. A pair of second curving units along the front-back direction that allow the absorber to curve in the inner direction in a convex shape is formed outboard of the first curving unit of the absorber in the widthwise direction. The top surface of the absorber that takes a convex shape in the inner direction due to the central curving unit is adapted to be in contact with the crotch of the wearer. A front end of the central curving unit is positioned posteriorly of a front end of at least one of the second curving units.

DESCRIPTION OF EMBODIMENTS

Next, embodiments of a disposable diaper 1 according to the present invention are explained with reference to drawings. More specifically, a first embodiment, a second embodiment, a third embodiment, and other embodiments are explained.

Note that in the description of the following drawings, the same or similar symbols are added to the same or similar portions. However, it must be taken into consideration that the drawings are schematic representations and are not drawn to scale unless otherwise specified. Moreover, the drawings do not necessarily reflect the actual dimensional relationships and ratios of components.

Therefore, the specific dimensions must be determined in view of the following explanation. Furthermore, relations or ratios among such dimensions may be different from one drawing to another.

First Embodiment

The disposable wearing article according to the present embodiment includes a central curving unit, a pair of first curving units, and a pair of second curving units, and a front end of the central curving unit is positioned posteriorly of a front end of at least one of the second curving units.

(1) Overall Schematic Configuration of the Disposable Wearing Article

Figure 1:
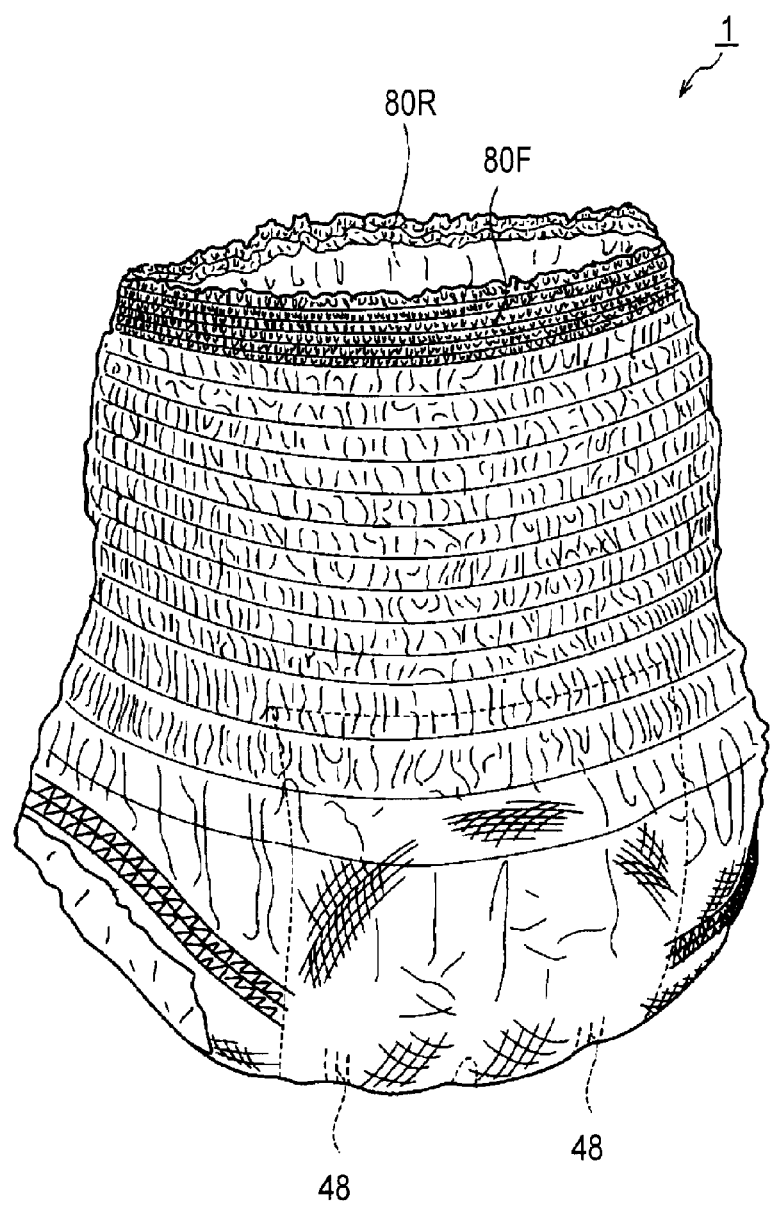
FIG. 1 is a schematic perspective view of a disposable diaper 1 according to a first embodiment.

FIG. 1 is a schematic perspective view of a disposable diaper 1 configuring the disposable wearing article in the present embodiment. As shown in FIG. 1, the disposable diaper 1 is a pants-type disposable diaper. The disposable diaper 1 includes a foreside exterior topsheet 70F, a backside exterior topsheet 70R, a foreside exterior backsheet 80F, a backside exterior backsheet 80R, and an exterior center sheet 100 constituting the exterior portion of the disposable diaper 1. An absorber 40 composed of cotton-like pulp and highly polymerized water absorbent polymer is provided at the inner side (skin contact surface side) of the foreside exterior topsheet 70F, the backside exterior topsheet 70R, and the exterior center sheet 100.

A central aperture 45 is formed in the center in the widthwise direction W of the absorber 40. Furthermore, a central elastic member 44 is provided so as to overlap the central aperture 45. A pair of side slits 42S is formed at both sides of the central aperture 45. A first elastic member 48 is provided so as to overlap at least partially with each of the side slits 42S. As a result of the elastic members and slits formed in the absorber 40, the absorber 40 is configured such that it curves when the disposable diaper 1 is worn. In the present embodiment, the central elastic member 44 configures a central curving unit, and the side slits 42S and the corresponding first elastic member 48 configure the second curving units.

Figure 2:
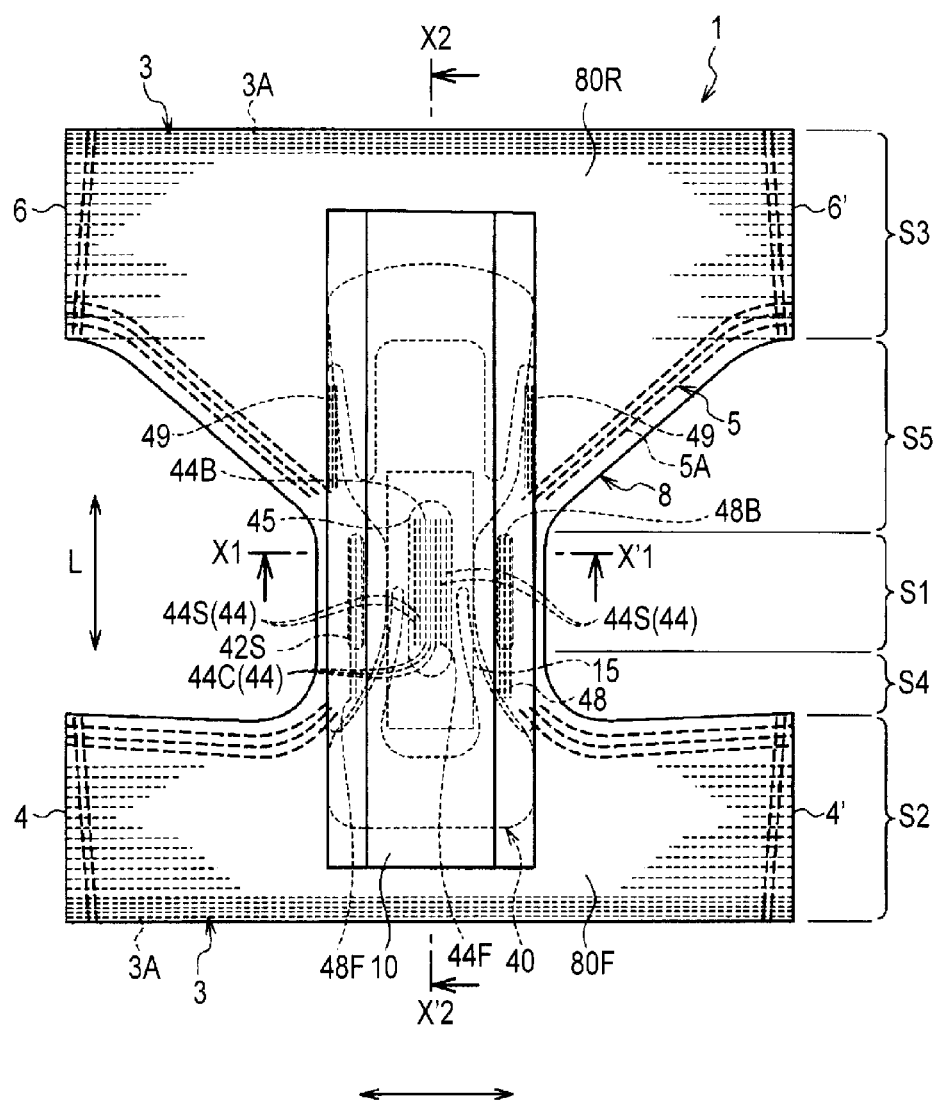
FIG. 2 is a developed plan view of the disposable diaper 1 according to the first embodiment.
Figure 3:
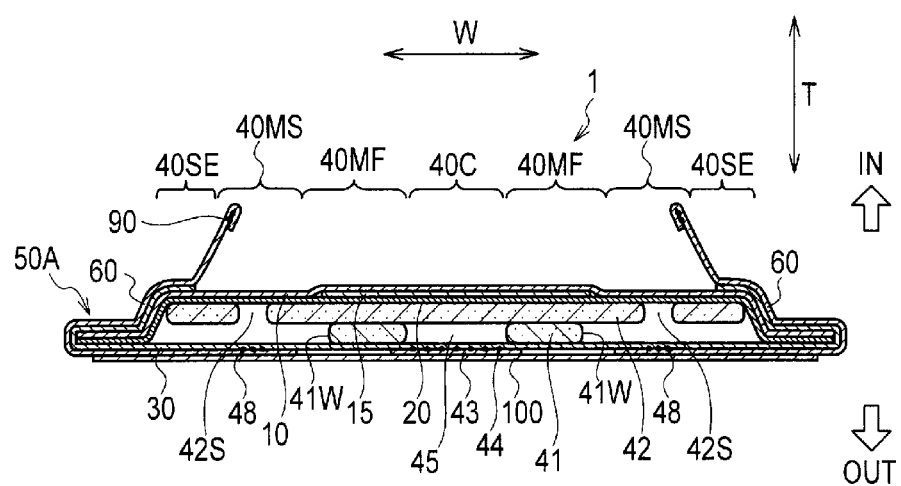
FIG. 3 is a cross-sectional view in the widthwise direction of the disposable diaper 1 taken along the X1-X'1 line shown in FIG. 2.
Figure 4:
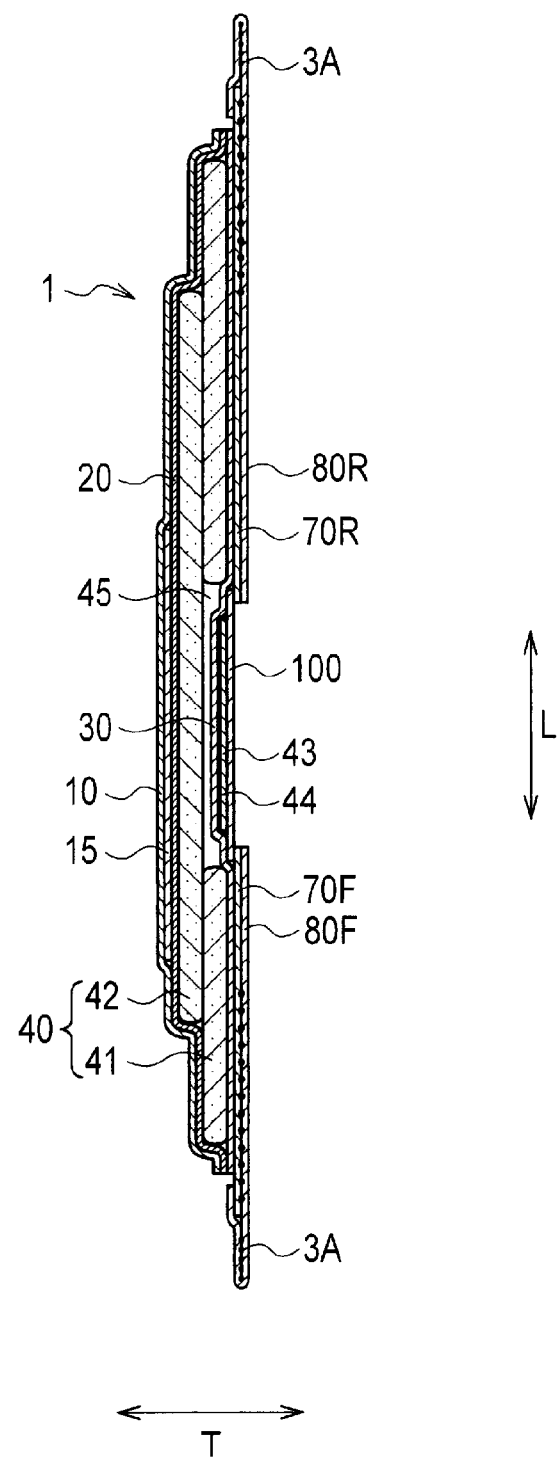
FIG. 4 is a cross-sectional view in the lengthwise direction of the disposable diaper 1 taken along the X2-X'2 line shown in FIG. 2.

FIG. 2 is a developed plan view of the disposable diaper 1 according to the present embodiment. FIG. 3 is a cross-sectional view in the widthwise direction of the disposable diaper 1 taken along the X1-X1' line shown in FIG. 2. FIG. 4 is a cross-sectional view in the lengthwise direction of the disposable diaper 1 taken along the X2-X2' line shown in FIG. 2.

As shown in FIG. 2, the disposable diaper 1 has a front waistline region S2 corresponding to the front waistline of the wearer, and a back waistline region S3 corresponding to the back waistline of the wearer. Furthermore, the disposable diaper 1 has a crotch region S1, a foreside middle inside leg region S4, and a backside middle inside leg region S5.

The crotch region S1 is the region corresponding the crotch of the wearer where the width between both legs becomes the narrowest when the wearer closes both legs. The foreside middle inside leg region S4 is positioned between the crotch region S1 and the front waistline region S2 in the lengthwise direction L of the absorber 40. The backside middle inside leg region S5 is positioned between the crotch region S1 and the back waistline region S3 in the lengthwise direction L.

Due to the fact that the front waistline edge 4 is joined with the back waistline edge 6, and at the same time, the front waistline edge 4' is joined with the back waistline edge 6', the disposable diaper 1 is formed as a pants type.

Waist gathers 3 are provided in the front waistline region S2 and the back waistline region S3. Waist gathers 3 have an elongated waist elastic member 3A, such as synthetic rubber, arranged to expand and contract along the widthwise direction W of the absorber 40. The waist elastic member 3A is joined with the foreside exterior topsheet 70F and foreside exterior backsheet 80F, as well as the backside exterior topsheet 70R and backside exterior backsheet 80R by an adhesive (for example, hot-melt adhesive) in an extended state along the widthwise direction W of the disposable diaper 1.

Leg gathers 5 are formed in the middle inside leg edge 8 of the backside exterior backsheet 80R. Leg gathers 5 are formed so as to run around the legs of the wearer. The leg gathers 5 have a plurality of leg elastic members 5A.

The disposable diaper 1 includes the topsheet 10, the absorber 40, a sidesheet 60, the foreside exterior topsheet 70F, the backside exterior topsheet 70R, the foreside exterior backsheet 80F, and the backside exterior backsheet 80R. Each of the topsheet 10, the absorber 40, the sidesheet 60, the foreside exterior topsheet 70F and the foreside exterior backsheet 80F, the backside exterior topsheet 70R and the backside exterior backsheet 80R, the exterior center sheet 100 and the foreside exterior topsheet 70F, and the exterior center sheet 100 and the backside exterior topsheet 70R is joined by an adhesive and thermal fusion bonding, for example.

The topsheet 10 forms a skin contact surface that can directly touch the skin of the wearer. The topsheet 10 is formed by a liquid-permeable sheet such as a hydrophilic nonwoven cloth and woven cloth, an aperture plastic film, and an aperture hydrophobic nonwoven cloth. A second sheet 15 is joined with the non-skin contact surface side of the topsheet 10.

An absorber topside covering sheet 20 is provided between the topsheet 10 and absorber 40. The absorber topside covering sheet 20 is formed by a liquid-permeable sheet such as a hydrophilic nonwoven cloth and woven cloth, an aperture plastic film, an aperture hydrophobic nonwoven cloth, and tissue.

An absorber backside covering sheet 30 is provided at the non-skin contact surface side, which is the surface opposite the topsheet 10 and absorber topside covering sheet 20, via the absorber 40. The absorber backside covering sheet 30 is formed by a sheet such as a liquid-impermeable film (for example, polyethylene).

The absorber 40 is covered with the absorber topside covering sheet 20 and the absorber backside covering sheet 30. The absorber 40 has a lengthwise direction L extending from the front waistline region S2 to the back waistline region S3, and a widthwise direction W perpendicular to the lengthwise direction L. Furthermore, the absorber 40 has an inner direction IN arranged for facing the wearer who wears the disposable diaper 1, and an outer direction OUT opposite the inner direction.

The sidesheets 60 overlap each other at the end of the sidesheets 60 in the widthwise direction. A side elastic member 90 is provided in an extended state along the lengthwise direction L in the portion where the sidesheets 60 overlap each other. The side elastic member 90 continues from the foreside middle inside leg region S4 up to the backside middle inside leg region S5 via the crotch region S1. The side elastic member 90 is formed by synthetic rubber, for example, having elasticity.

The sidesheet 60 is provided so as to package the topsheet 10, the absorber topside covering sheet 20, and the absorber backside covering sheet 30 as one package at both ends in the widthwise direction W of the absorber 40. The sidesheet 60 is formed by a sheet such as a liquid-impermeable nonwoven cloth, and a leakage-preventing wall that prevents the side leakage of excretions is configured by the sidesheet 60 and the side elastic member 90.

The exterior topsheet includes a foreside exterior topsheet 70F formed in the front waistline region S2 and the foreside middle inside leg region S4, and the backside exterior topsheet 70R formed in the back waistline region S3 and the backside middle inside leg region S5. The exterior center sheet 100 is arranged in the lengthwise direction between the foreside exterior topsheet 70F and the backside exterior topsheet 70R. The front end of the exterior center sheet 100 is joined with the rear end of the foreside exterior topsheet 70F, and the rear end of the exterior center sheet 100 is joined with the front end of the backside exterior topsheet 70R. As for the foreside exterior topsheet 70F and the backside exterior topsheet 70R, the width in the widthwise direction W is formed larger in the front waistline region S2 and the back waistline region S3 that than in the other regions. The foreside exterior topsheet 70F and the backside exterior topsheet 70R can be formed by an air-through nonwoven cloth, a spunbond nonwoven cloth, an SMS (spunbond-meltblown-spunbond) nonwoven cloth, and a water-resistive film.

The foreside exterior backsheet 80F is provided at the non-skin contact surface side than the foreside exterior topsheet 70F in the front waistline region S2. The backside exterior backsheet 80R is provided at the non-skin contact surface side than the backside exterior topsheet 70R in the back waistline region S3. One end of the foreside exterior backsheet 80F (backside exterior backsheet 80R) in the lengthwise direction L is folded back in the skin contact surface side and is provided so as to encompass the ends of the foreside exterior topsheet 70F (backside exterior topsheet 70R) in the lengthwise direction L. The foreside exterior backsheet 80F can be formed by an air-through nonwoven cloth, a spunbond nonwoven cloth, an SMS nonwoven cloth, and a water-resistive film.

The central elastic member 44 is provided along the lengthwise direction L and is provided at a position overlapping with the central aperture 45 in the thickness direction T of the disposable diaper 1. The central elastic member 44 can be formed so as to overlap the absorber 40 along the lengthwise direction L such that the absorber 40 curves in a convex shape in use towards the wearer.

Each first elastic member 48 is provided at a position overlapping a side slit 42S (described later) in the thickness direction T of the disposable diaper 1, in the lengthwise direction L. Each first elastic member 48 is formed so as to overlap the absorber 40 along the lengthwise direction L such that the absorber 40 curves in a convex shape towards the wearer.

The central elastic member 44 and the first elastic members 48 are provided in an extended state at the non-skin contact surface side of the absorber backside covering sheet 30. Furthermore, an elastic member covering sheet 43 is provided at the non-skin contact surface side of the central elastic member 44, and the central elastic member 44 is joined between the absorber backside covering sheet 30 and the elastic member covering sheet 43 by an adhesive. Moreover, a sidesheet 60 is provided at the non-skin contact surface side of the first elastic members 48, and each first elastic member 48 is joined between the absorber backside covering sheet 30 and the sidesheet 60 by an adhesive. Note that the central elastic member 44 and the first elastic members 48 may be joined with the topsheet 10, or with the foreside exterior topsheet 70F and backside exterior topsheet 70R.

Furthermore, the front end 44F of the central elastic member 44 is arranged posteriorly of the front end 48F of each first elastic member 48. That is, the front end of the central curving unit is provided posteriorly of the front end of the second curving unit. According to such a configuration, an appropriate gap can be formed easily at the anterior side of the wearer in the crotch of the wearer, and the deterioration in the wearing comfort can be alleviated due to compression of the foreside of the crotch of the wearer by the curved absorber.

On the other hand, the rear end 48B of each first elastic member 48 is arranged anteriorly of the rear end 44B of the central elastic member 44. That is, the rear end of the second curving unit is provided anteriorly of the rear end of the central curving unit. If the second curving unit extends too much posteriorly, the second curving unit might extend up to the proximity of the buttocks, and it might be difficult for the absorber 40 to run along the curve of the buttocks. However, according to aforementioned arrangement, the wearing article can easily form into a smooth curve, the wearing article can be arranged along the buttocks, and an appropriate gap can be maintained between the wearing article and the skin. Thus, excretions, such as urine and stool excreted in the gap between the wearing article and the skin can be collected temporarily, and the leakage of excretions, such as fluid leakage can be prevented. Furthermore, because the wearing article takes a shape along the buttocks, the contour of the wearing article takes a shape along the body, and the appearance can be kept good.

Examples of a raw material of the central elastic member 44 include, for example, synthetic rubber such as styrene-butadiene, butadiene, isoprene, and neoprene, natural rubber, EVA, elastic polyolefin, spandex, and foamed polyurethane. Besides these, an elastic sheet such as an elastic nonwoven cloth can be used as the raw material of the central elastic member 44.

In the first embodiment, the central elastic member 44 has a total of seven elastic members, including three central portion elastic members 44C arranged in parallel across approximately 10 mm in the widthwise direction W, and two central auxiliary elastic members 44S arranged in parallel, and on each side of the central portion elastic members 44C in the widthwise direction. The length of the central elastic member 44 is approximately 120 mm in the lengthwise direction L. Three central portion elastic members 44C are each extended and fixed with a thickness of 620 dtex and an extension magnitude of 2.5 times, and the central auxiliary elastic members 44S each are extended and fixed with a thickness of 620 dtex and an extension magnitude of 1.8 times in a particular configuration. The material of the central elastic member 44 is spandex. In the state prior to curving of the absorber in a convex shape, each central portion elastic member 44C has a stress more than a stress of each central auxiliary elastic member 44S. Thus, due to the central elastic member 44, the absorber 40 curves in a better way in a convex shape in the inner direction IN, that is, the absorber 40 curves in a convex shape towards the wearer. Furthermore, the curve at the crest of the convex shape takes a gentle slope, and the area sticking with the skin can be increased. The extension magnitude of each central elastic member 44C is desired to be between 1.4 times and 3.0 times, and the extension magnitude of each central auxiliary elastic member 44S is desired to be between 1.2 times and 2.8 times.

In the first embodiment, three first elastic members 48 are arranged in parallel on each side of the disposable diaper 1 in the widthwise direction W. The material of the first elastic members 48 is spandex. Three first elastic members 48 each are extended and fixed with a thickness of 620 dtex and an extension magnitude of 2.0 times in a particular configuration. Note that each first elastic member 48 is configured such that in the state prior to curving of the absorber in a convex shape, its stress is less than that of the central elastic member 44. In other words, the total stress of all three first elastic members 48 on each side is less than the total stress of all seven central elastic members 44C, 44S. The state prior to curving of the absorber in a convex shape is the state in which the wearing article is extended flatly as shown in FIG. 2. By configuring each first elastic member 48 such that its stress is lower than that of the central elastic member 44, the height of the convex-shaped portion formed by the central elastic member 44 becomes more than that of the convex-shaped portion formed by each first elastic member 48. Thus, at the time of wearing, the convex-shaped portion in the central region can be stuck to the excretory opening side of the wearer.

The stress of the elastic member, for example, can be measured as follows: (1) The material holding the elastic members in between is cut such that all the elastic members forming the convex-shaped portion(s) are included in the widthwise direction. More specifically, from the wearing article according to the present embodiment, a test piece of 13-mm width×100-mm length that hold the three central elastic members or the three first elastic members arranged in an interval of 5 mm, in an elongated state such that there is no sagging, is cut out. In the elongated state, a mark is put at 10 mm from either end in the longitudinal direction of the test piece. A tensile tester made by Instron Japan Co., Ltd. (for example, model No. 5564) or an autograph made by Shimadzu Corporation (for example, model No. AGS-1kNG) can be used to measure the elongation stress.

(2) The test piece prepared at (1) is held in between the upper chuck, such that one of the marks is at the inner end of the upper chuck, and the lower chuck, such that the other mark is at the inner end of the lower chuck. The length of the test piece between the chucks is 80 mm. Note that if the effective length of the gathers of the elastic member is less than 100 mm, a length that is 20 mm shorter than the shortest length from among the effective lengths of the gathers of the elastic members is set as the length of the test piece between the chucks. The initial distance between chucks is set shorter than the length (natural length) when the test piece is relaxed such that no external tension is exerted on the test piece. In order to be alienated from each other, the chucks pull the test piece in the vertical direction under a condition of 100 mm/min, and elongate the test piece.

(3) By assuming the length of the test piece between the chucks as 100% when the material holding the elastic members in between is elongated without any sagging, the test piece is elongated from the initial distance until its length between the chucks becomes 90%, and then the elongation stress of the test piece is measured for that point of time and set as the stress of the elastic member. That is, in the above embodiment, the elongation stress is measured when the test piece is elongated until its length becomes 90% that is 72 mm, of the 100% length of 80 mm.

Furthermore, second elastic members 49 are provided posteriorly of the central elastic member 44 and the first elastic members 48, and outboard of the central elastic member 44 and the first elastic members 48 in the widthwise direction. Each second elastic member 49 is provided at a position overlapping the absorber 40 in the thickness direction T of the disposable diaper 1. The second elastic members 49 are configured so as to shrink the wearing article near the buttocks in the inner direction IN side to shape the wearing article along the buttocks. Furthermore, by shaping the wearing article along the buttocks, the contour of the wearing article takes a shape along the body, and the appearance can be kept good. The material of the second elastic members 49 is spandex, and it is extended and fixed with a thickness of 780 dtex and an extension magnitude of 2.3 times in a particular configuration.

The first elastic members 48 and the second elastic members 49 are provided such that they do not overlap when seen in the widthwise direction W. That is, the first elastic members 48 and the second elastic members 49 are alienated in the lengthwise direction L. Each first elastic member 48 forms the second curving unit for forming the absorber 40 in a convex shape in the inner direction IN. A trough is provided with respect to a crest formed by the second curving unit, and outboard of each first elastic member 48 in the widthwise direction. The second elastic members 49 are arranged outboard of the first elastic members 48 in the widthwise direction, and bias the absorber 40 in the inner direction IN. If the first elastic members 48 and the second elastic members 49 are arranged adjacent to each other, the trough provided with respect to the crest formed by the second curving unit is pushed up by the biasing force of the adjacent second elastic member 49, and it might become difficult to maintain the convex shape formed by the second curving unit. Thus, it is desired that the first elastic members 48 and the second elastic members 49 be provided such that they do not overlap when seen in the widthwise direction W. Furthermore, if the first elastic members 48 and the second elastic members 49 overlap when seen in the widthwise direction W, the length of the overlapping region in the lengthwise direction L is desired to be below 20 mm.

Furthermore, the absorber topside covering sheet 20 may also be configured such that it is joined with the absorber backside covering sheet 30 in the portion in which the side slits 42S are formed. By configuring in this way, the closure of the side slits 42S due to a deformation of the absorber 40, and the deviation of the absorber 40 from the absorber topside covering sheet 20, etc., can be prevented. Furthermore, in cases where the absorber 40 absorbs the liquid and swells up, the closure of the side slits 42S can be prevented, and therefore, a convex-shaped portion can be formed properly by the side slits 42S.

Note that each member configuring the disposable diaper 1 may, for example, use the respective materials described in the Japanese Published Unexamined Application No. 2006-346439, which is incorporated by reference herein in its entirety.

Figure 5:
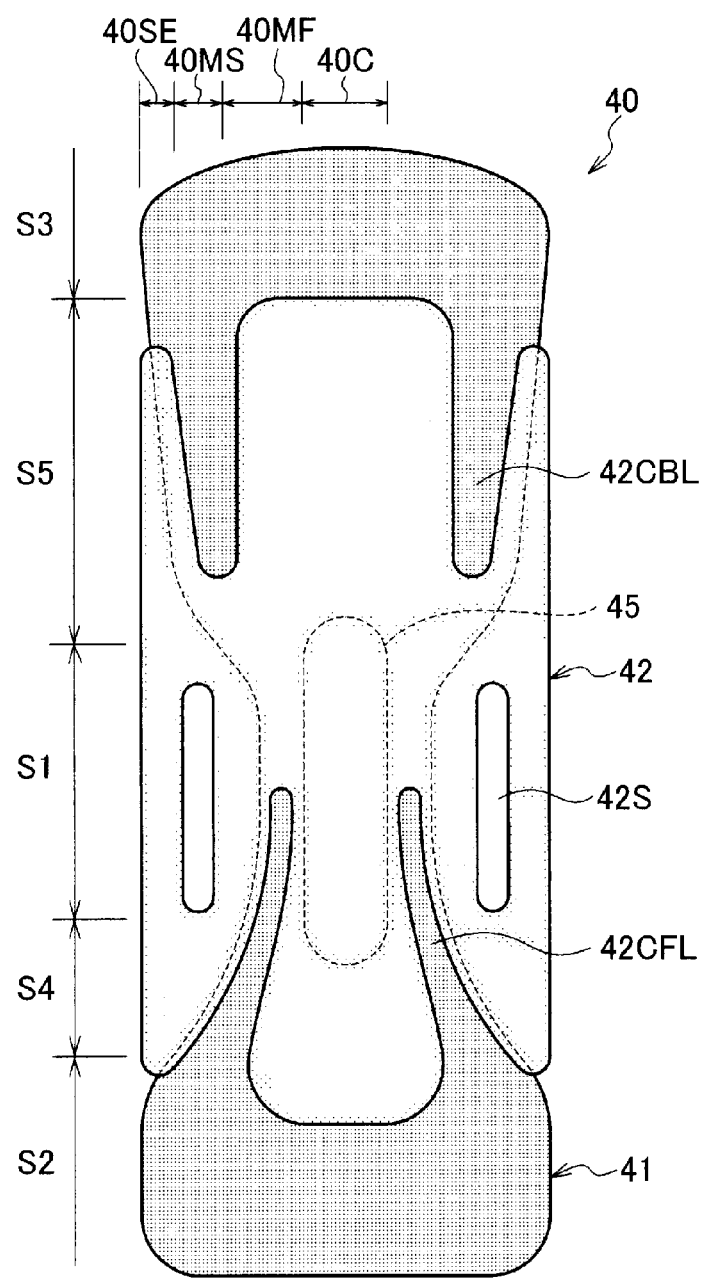
FIG. 5 is a plan view of an absorber 40 according to the first embodiment.
Figure 6:
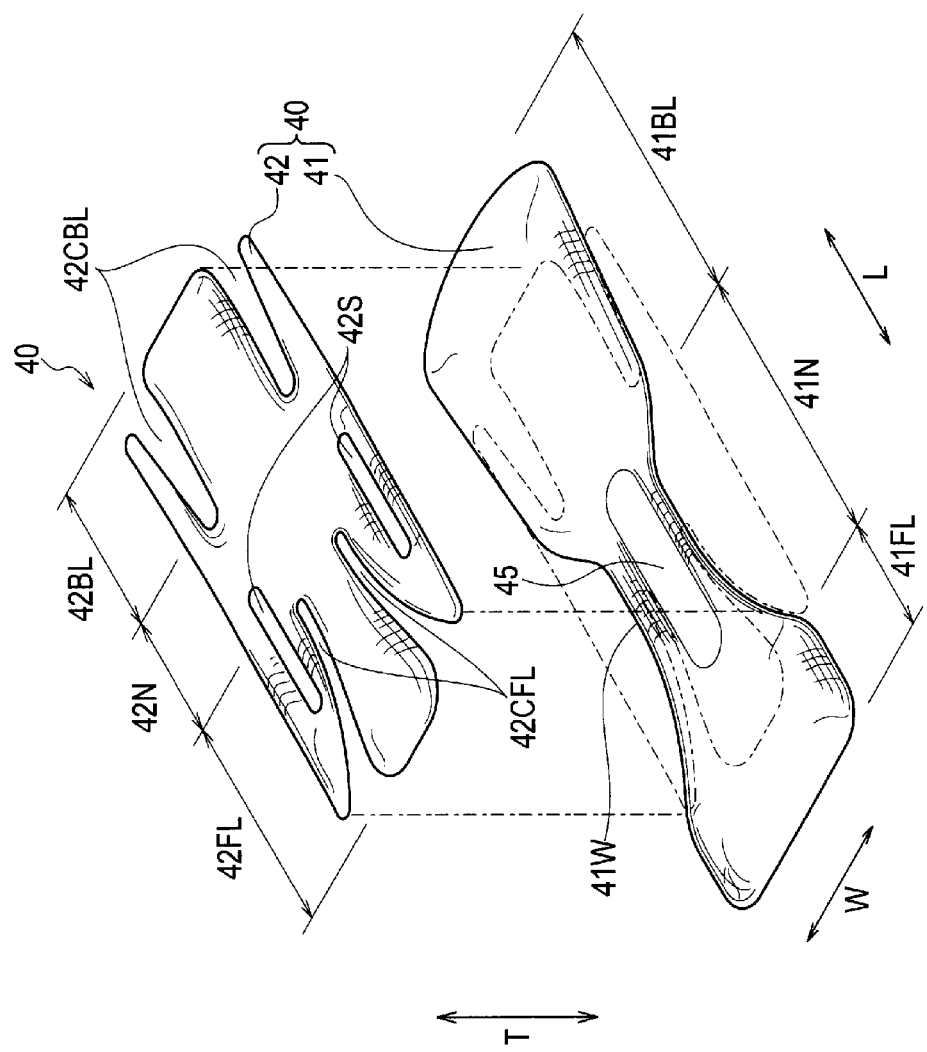
FIG. 6 is an exploded, perspective view of the absorber 40 according to the first embodiment.

(2) Structure of the Absorber:

FIG. 5 is a plan view of the absorber 40 and FIG. 6 is an exploded, perspective view of the absorber 40. As shown in FIG. 5 and FIG. 6, the absorber 40 has a first absorbent layer (also referred to herein as first layer) 41, and a second absorbent layer (also referred to herein as second layer) 42 overlapping the first layer 41. The first layer 41 is positioned at the non-skin contact surface side of the wearer, and the second layer 42 is positioned at the skin contact surface side of the wearer.

The first layer 41 and the second layer 42 are configured by cotton-like pulp and highly polymerized water absorbent polymer (SAP). The first layer 41 is formed by mixing together 270 g/m² of pulp and 170 g/m² of SAP, and its thickness in the thickness direction T is approximately 3.0 mm in a particular configuration. The second layer 42 is formed by mixing together 400 g/m² of pulp and 240 g/m² of SAP, and its thickness in the thickness direction T is approximately 4.4 mm in a particular configuration. That is, the thickness of the portion where the first layer 41 and the second layer 42 overlap is approximately 7.4 mm. Note that it is desired that the first layer 42 contain 100 to 500 g/m² of pulp and 0 to 500 g/m² of SAP.

As shown in FIG. 2 and FIG. 6, the first layer 41 has a narrow part 41N that is concave towards the center of the widthwise direction W and has a predetermined width in the widthwise direction W, and a wide part 41FL and wide part 41BL formed on both ends of the narrow part 41N in the lengthwise direction L. The narrow part 41N is formed in the crotch region S1. Furthermore, the wide part 41FL is formed in the front waistline region S2, and the wide part 41BL is formed in the back waistline region S3. The side ends of the narrow part 41N and the side ends of the wide part 41FL and the wide part 41BL are connected by a curve, and the first layer 41 has an hourglass-type flat shape.

Furthermore, a central aperture 45 is formed in the center of the widthwise direction W of the first layer 41. The central aperture 45 has a longitudinally elongated shape extending along the lengthwise direction L, and is formed across the crotch region S1, the foreside middle inside leg region S4, and the backside middle inside leg region S5. The length of the central aperture 45 is approximately 180 mm and its width is approximately 40 mm in a particular configuration. By forming the central aperture 45 in this way, the central portion 40C can be curved easily in a convex shape in the inner direction IN toward the wearer. Furthermore, by increasing the diffusibility of the bodily fluid in the front-back direction of the absorber and by diffusing the bodily fluid in a wide range, the absorption performance can be improved.

Furthermore, the density of the narrow part 41N of the first layer is configured such that it is higher than the density of the wide part 41FL of the first layer 41, and also higher than the density of the wide part 41BL of the first layer 41. Moreover, the density of the narrow part 41N of the first layer 41 is higher than the density of the second layer 42. Thus, the narrow part 41N of the first layer 41 has a higher rigidity than the other portions of the first layer 41 and the second layer 42.

The second layer 42 has a notched part 42FL in which a notch is formed from the front end towards the center, a notched part 42BL in which a notch is formed from the rear end towards the center, and a central part 42N positioned between the notched part 42FL and the notched part 42BL.

The length of the second layer 42 in the widthwise direction is longer than that of the narrow part 41N of the first layer 41, and is almost the same as the length of the widest portion in the wide part 41BL and the wide part 41FL of the first layer 41. A notch 42CFL and a notch 42CBL extending towards the center from both end parts in the front-back direction are formed in the second layer.

A pair of side slits 42S is formed in the second layer 42. The side slits 42S are formed in the absorber 40 along the lengthwise direction L such that the absorber 40 curves in a convex shape in the same direction as the central aperture 45. The length of the side slits 42S is shorter than that of the central aperture 45, and the width of the side slits 42S is narrower than that of the central aperture 45. More specifically, the length of the side slits 42S is approximately 110 mm and its width is approximately 15 mm in a particular configuration.

The notch 42CFL is formed across the foreside middle inside leg region S4 and the front waistline region S2, and the notch 42CBL is formed in the backside middle inside leg region S5. The aperture shape of the notch 42CFL extends in the inner side of the widthwise direction towards the center.

Both outer edges in the widthwise direction of the notch 42CFL have almost the same width as both outer edges in the widthwise direction of the narrow part 41N of the first layer 41 in the crotch region S1 and the foreside middle inside leg region S4. According to such a configuration, the width of the anterior portion of the absorber, when the legs are closed and folded in a state of wearing the wearing article, can be reduced. Thus, the thickness of the absorber at the foreside of the body of the wearer can be reduced, and the discomfort at the crotch of the wearer can be reduced.

Both outer edges in the widthwise direction of the notch 42CBL have almost the same width as both outer edges in the widthwise direction of the wide part 41BL of the first layer 41 in the backside middle inside leg region S5. According to such a configuration, when the absorber gets swollen in a state when it absorbs the bodily fluid, a gap is formed easily between the absorber and the skin of the wearer. Moreover, by providing the notch 42CBL, the bodily fluid can be transferred smoothly from the second layer 42 to the first layer 41, and the performance of the absorber can be harnessed effectively.

In the crotch region S1, the outer ends 41W in the widthwise direction of the first layer 41 are arranged along the front-back direction. Outside the outer ends 41W, the absorber 40 is configured only by the second layer 42. Inside the outer ends 41W, except for the portion in which the central aperture 45 is formed, the absorber 40 is configured by the first layer 41 and the second layer 42. Thus, the rigidity and thickness of the absorber 40 change at the boundary defined by the outer ends 41W of the first layer 41. In the present embodiment, the absorber curves with the outer ends 41W of the first layer where the rigidity, thickness etc., change, as the boundary. That is, the outer ends 41W of the first layer 41 configure the first curving unit. Thus, according to the configuration in which a convex-shaped portion is formed with the outer ends 41W of the first layer, where the thickness of the absorber 40 changes, as the boundary, in comparison with the configuration in which a convex-shaped portion is formed by slits, the need for forming an aperture by slits in the proximity of the convex-shaped portion does not exist, and therefore, a convex-shaped portion can be formed while maintaining the absorption performance. Note that the outer ends 41W in the widthwise direction of the first layer 41 are edge sides along the front-back direction of the first layer. Thus, the first curving unit is formed along the front-back direction.

The absorber 40 thus configured by the first layer 41 and the second layer 42 has a central portion 40C, first intermediate portions 40MF, second intermediate portions 40MS, and side end portions 40SE, as shown in FIG. 3. The central portion 40C is formed in the center of the absorber 40 in the widthwise direction W. The intermediate portion is positioned between the central portion 40C and the side end portions 40SE. The intermediate portion has first intermediate portions 40MF and second intermediate portions 40MS. The first intermediate portions 40MF are positioned between the central portion 40C and the second intermediate portions 40MS. A convex-shaped portion is formed by a first curving unit in the first intermediate portions 40MF. The second intermediate portions 40MS are positioned between the first intermediate portions 40MF and the side end portions 40SE. A convex-shaped portion is formed by a second curving unit in the second intermediate portions 40MS. The side end portions 40SE are formed at the side ends of the absorber 40 in the widthwise direction W.

In the present embodiment, the central portion 40C, the second intermediate portions 40MS, and the side end portions 40SE are formed only by the second layer 42 in the crotch region S1. On the other hand, the first intermediate portions 40MF have a portion formed only by the second layer 42, and a portion formed by the first layer 41 and the second layer 42. Therefore, the thickness of the absorber 40 in a part of the first intermediate portions 40MF is more than the thickness of the absorber 40 in the central portion 40C and the side end portions 40SE.

The thickness of the absorber 40 is measured by holding the portion to be measured in the thickness measuring gauge in a state when it has been extended to the product length and product width of the absorber 40 (that is, in a flat state such that no creases are formed). A thickness gauge manufactured by PEACOCK (measuring portion: 5-mm diameter, pressure during measurement: 163 g/cm$^2$), for example, can be used as the usable measurement device.

In the present embodiment, the first layer 41 and the second layer 42 are formed as one part by being pressed along the thickness direction T. Note that the first layer 41 and the second layer 42 may also be formed as one part by an adhesive and thermal fusion bonding. Furthermore, in the absorber 40, the first layer 41 is positioned at the non-skin contact surface side and the second layer 42 is positioned at the skin contact surface side, but the second layer 42 may be positioned at the non-skin contact surface side and the first layer 41 may be positioned at the skin contact surface side.

(3) Shape Change of the Absorber

Figure 7:
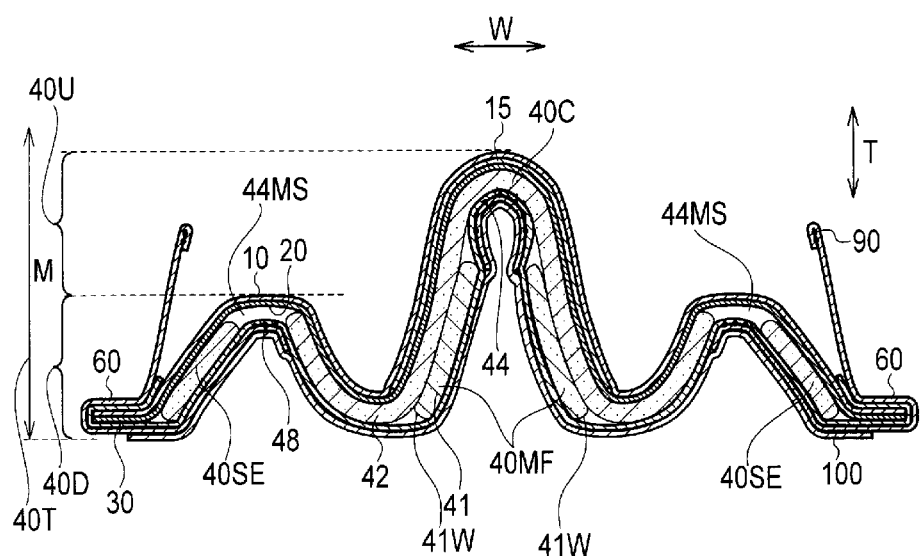
FIG. 7 is a cross-sectional view schematically showing the wearing state of the disposable diaper 1 according to the first embodiment.

FIG. 7 is a cross-sectional view (with reference to the X1-X'1 line of FIG. 1) schematically showing the wearing state of the disposable diaper 1. As shown in FIG. 7, when the disposable diaper 1 is worn, the absorber 40 curves with (i) the outer ends 41W in the widthwise direction of the first layer 41, (ii) the central elastic member 44, and (iii) the first elastic members 48 as the base points, and the cross-sectional shape along the widthwise direction W of the disposable diaper 1 deforms to a wavy shape. As a result, the top surface of the absorber 40 that takes a convex shape in the inner direction IN due to the central elastic member 44 is adapted to come in contact with the crotch of the wearer. Furthermore, the central portion 40C is positioned in the upper region 40U in the proximity of the body of the wearer from the virtual line M that bisects the height 40T of the absorber 40 in the deformed state. On the other hand, the first intermediate portions 40MF, the second intermediate portions 40MS, and the side end portions 40SE are positioned in the lower region 40D separated from the body of the wearer from the virtual line M.

The central portion 40C in which a convex-shaped portion is formed by the central curving unit is configured only by the second layer 42, and its thickness is comparatively less. In a first intermediate portion 40 MF between the convex-shaped portion due to the central curving unit and the convex-shaped portion due to the first curving unit, the first layer and the second layer are overlapping, and its thickness is comparatively more. Furthermore, the density of the crotch region S1 of the first layer 41 is comparatively higher than that of other regions in the first layer 41, and the rigidity is higher. The convex-shaped portion due to the central curving unit can be supported by a portion between the central curving unit and the first curving unit where the rigidity is higher, and the stability of the convex shape due to the central curving unit can be improved.

Note that the side edges 50A (leg standing gathers) including the side elastic members 90 are desired to be positioned at a higher position than the central portion 40C in the thickness direction T of the figure, that is, at the wearer's side.

Figure 8:
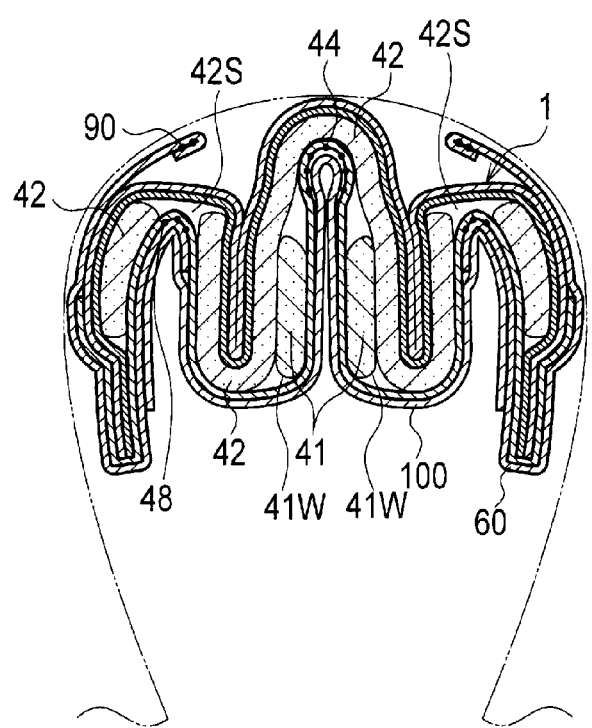
FIG. 8 is a cross-sectional view (when the wearer's legs are closed) schematically showing the wearing state of the disposable diaper 1 according to the first embodiment.

FIG. 8 is a cross-sectional view (with reference to the X1-X'1 line of FIG. 2) schematically showing the wearing state of the disposable diaper 1 when the wearer closes his/her legs. Note that the virtual line in the figure shows the crotch and both legs of the wearer.

As shown in FIG. 8, when the wearer closes both legs, the cross-sectional shape of the disposable diaper 1 changes from the state shown in FIG. 7 to the state shown in FIG. 8. As shown in FIG. 8, when the wearer closes both legs, the central portion 40C and the second intermediate portions 40MS are positioned such that they are in contact with the crotch of the wearer. On the other hand, the first intermediate portions 40MF and the side end portions 40SE are positioned downward (crotch side) from the central portion 40C.

According to the disposable diaper 1 explained above, a central elastic member 44 and first elastic members 48 formed in the absorber 40 such that the absorber 40 curves in a convex shape in the inner direction IN, and a pair of side slits 42S formed in the absorber 40 such that the absorber 40 curves in a convex shape in the outer direction OUT are included. The distance between the central elastic member 44 configuring the central curving unit and the outer ends 41W of the first layer 41 configuring the first curving unit in the widthwise direction is longer than the distance between the outer ends 41W and the first elastic member configuring the second curving unit in the widthwise direction. Therefore, the height of the convex-shaped portion of the central portion 40C is more than the height of the convex-shaped portion of the second intermediate portion 40MS. Thus, when wearing the disposable diaper 1, the central portion 40C that forms a convex shape facing the excretory opening of the wearer easily comes into contact with the excretory opening. Furthermore, because a concave portion is formed in the first intermediate portions 40MF, the excretions easily enters the concave portion, and a direct contact between the skin of the wearer and the excretions can be prevented.

Particularly, because a central aperture 45 is formed in the portion of the central elastic member 44, and side slits 42S are formed in the absorber 40, as compared to the case in which a thin portion is formed in the absorber 40, which is treated as a convex-shaped portion, the absorber 40 curves easily even when it absorbs liquid and swells up. Furthermore, the cross-sectional shape when the disposable diaper 1 is worn and the absorber 40 is deformed takes a tapered form that narrows towards the crotch of the wearer from the inside leg region, which makes it difficult to feel the discomfort of the disposable diaper getting stuck in the gap of the crotch of the wearer.

Furthermore, the convex-shaped portion formed by the central curving unit is configured only by the second layer, and has a lesser thickness than the portion configured by stacking the first layer 41 and the second layer 42. That is, the convex-shaped portion formed by the central curving unit has low thickness and high height, and therefore, it easily enters the narrow gap of the crotch of the wearer, and easily comes into contact with the excretory opening. Thus, for example, because the urination opening and the absorber contact, the excreted urine can be absorbed fast.

Finally, the configuration is such that in the crotch region S1, the density of the absorber 40 positioned between the first curving unit and the central curving unit becomes more than the density of the absorber 40 of the central portion 40C and the side end portions 40SE. That is, in the widthwise direction, the absorber 40 has the highest rigidity between each first curving unit and the central curving unit. The absorber 40 positioned between the first curving unit and the central curving unit is positioned outboard of the central curving unit in the widthwise direction, and supports the central convex-shaped portion. Due to the fact that the density of the absorber 40 positioned between the first curving unit and the central curving unit is high, the central curving unit can be maintained in an erect state even when the central curving unit comes in contact with the excretory opening and is pressed by the body of the wearer. Note that because the thickness of the central portion 40C projecting out at the side of the excretory opening of the wearer is less and the rigidity is less, even when the convex-shaped portion in the center is supported by high density portions of the absorber 40 positioned between the first curving unit and the central curving unit, the feeling of pressure to the wearer is less, and deterioration in the wearing comfort can be prevented.

That is, according to the disposable diaper 1, the absorption performance can be increased by placing the absorber close to or in contact with the excretory opening. Furthermore, the fitting in the backside of the body can be improved while maintaining an appropriate gap in the foreside of the body, and the wearing comfort can be improved.

In the present embodiment, the absorber 40 has a two-layer structure including the first layer 41 and the second layer 42, however, the absorber 40 of the wearing article according to the present embodiment may also be configured by only a single absorbent layer, and also by three or more absorbent layers.

Second Embodiment

Next, the configuration of the absorbers 40G, 40H, 40I, and 40J of a disposable diaper according to a second embodiment is explained with reference to drawings. Note that the same symbols are used to denote portions similar to those of the first embodiment, and the differences between the embodiments are mainly explained below.

Figure 9:
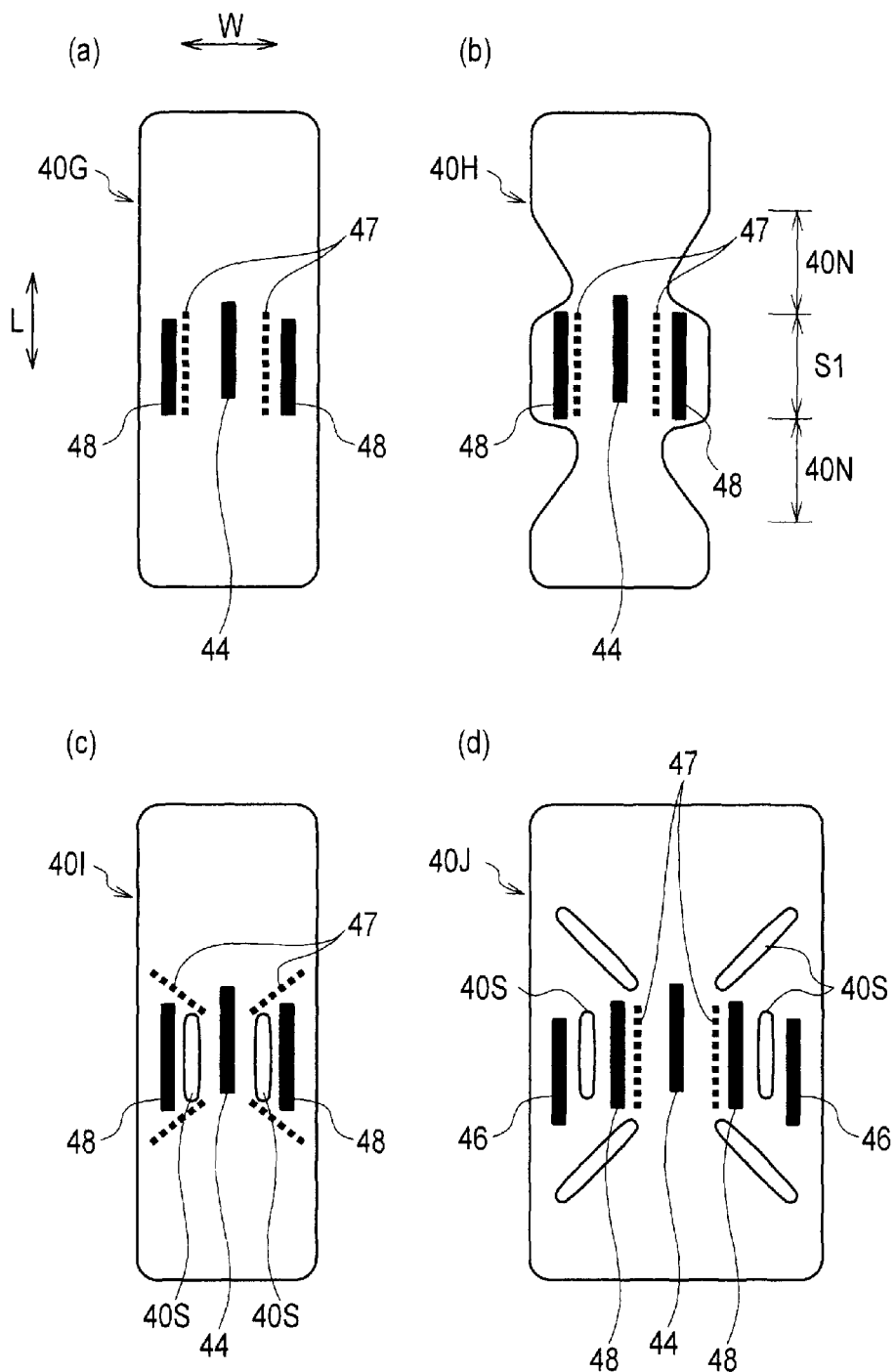
FIG. 9 is a plan view of an absorber of the disposable diaper 1 according to a second embodiment.

FIG. 9 is a plan view of the absorbers of a disposable diaper according to the second embodiment. An absorber according to the second embodiment is configured by only a first layer, and the configuration of the curving units is different from the absorber according to the first embodiment.

An absorber 40G shown in FIG. 9 (a) is formed with five curving units. A central curving unit and a pair of second curving units are configured by a central elastic member 44 and first elastic members 48 along the lengthwise direction, and the absorber takes a convex shape in the inner direction IN at the central and second curving units. Furthermore, in the widthwise direction, compressed portions 47 where the absorber is compressed in the thickness direction are formed between the central elastic member 44 and the first elastic members 48. A pair of first curving units is configured by the compressed portions 47, and the absorber takes a convex shape in the outer direction OUT at the first curving units. Note that the compressed portions 47 may be formed by embossing.

In an absorber 40H shown in FIG. 9 (b), the configuration of the curving units is similar to the absorber 40G shown in FIG. 9 (a), but the contour of the absorber is different. The absorber 40H has a pair of narrow parts 40N with narrow lengths in the widthwise direction and located at the outer sides in the lengthwise direction L (i.e., forward and rearward) with respect to the crotch region S1. A curving unit is arranged between the pair of narrow parts 40N in the lengthwise direction. Thus, by providing narrow parts 40N at the outer sides in the lengthwise direction of the crotch region S1 in which a curving unit is formed, roughening and deformation due to the curving unit can be prevented from extending to the front-back direction from the crotch region S1. Thus, for example, in the buttocks, etc., positioned rearward in the front-back direction with respect to the crotch of the wearer, the wearing article can easily be arranged along the body and the fitting can be improved further.

An absorber 40I shown in FIG. 9 (c) is formed by five curving units. A central curving unit and a pair of second curving units are configured by a central elastic member 44 and first elastic members 48 along the lengthwise direction, and the absorber takes a convex shape in the inner direction IN at the central and second curving units. Furthermore, in the widthwise direction, slits 40S extending in the lengthwise direction are formed between the central elastic member 44 and the first elastic members 48. A pair of first curving units is configured by the slits 40S, and the absorber takes a convex shape in the outer direction OUT at the first curving units.

At both outer sides in the lengthwise direction with respect to the crotch region of the absorber 40I, compressed portions 47 are formed to extend obliquely outwardly in both the lengthwise direction and the widthwise direction. Thus, by providing the compressed portions 47 at the outer sides in the lengthwise direction of the curving units, the formation of a convex-shaped portion extending in the front-back direction beyond the compressed portions 47 can be prevented.

In the absorber 40J shown in FIG. 9 (d), nine curving units are formed. First curving units, second curving units, third curving units, and fourth curving units are formed from the central curving unit towards the outer side in the widthwise direction. The central curving unit, the pair of second curving units, and the fourth curving units are configured by a central elastic member 44, first elastic members 48, and third elastic members 46 along the lengthwise direction, and the absorber takes a convex shape in the inner direction IN at the central, second and fourth curving units. In the widthwise direction, compressed portions 47 is formed between the central elastic member 44 and the first elastic members 48 extending in the lengthwise direction L, and slits 40S are formed between the first elastic members 48 and the third elastic members 46. The pair of first curving units is configured by the compressed portions 47, and the pair of third curving units is configured by slits 40S, and the absorber takes a convex shape in the outer direction OUT at the first and third curving units.

At the outer sides in the lengthwise direction with respect to the crotch region of the absorber 40J, slits 40S are formed to extend obliquely outwardly in both the lengthwise direction and the widthwise direction. Thus, by providing the slits 40S at the outer sides in the lengthwise direction of the curving units, the formation of a convex-shaped portion formed due to the curving units and extending in the front-back direction beyond the slits 40S can be prevented.

Third Embodiment

Next, the configuration of the absorbers 40K, 40L, 40P, and 40Q of a disposable diaper according to a third embodiment is explained with reference to drawings. Note that the same symbols are used to denote portions similar to those of the first embodiment, and the differences between the embodiments are mainly explained below.

Figure 10:
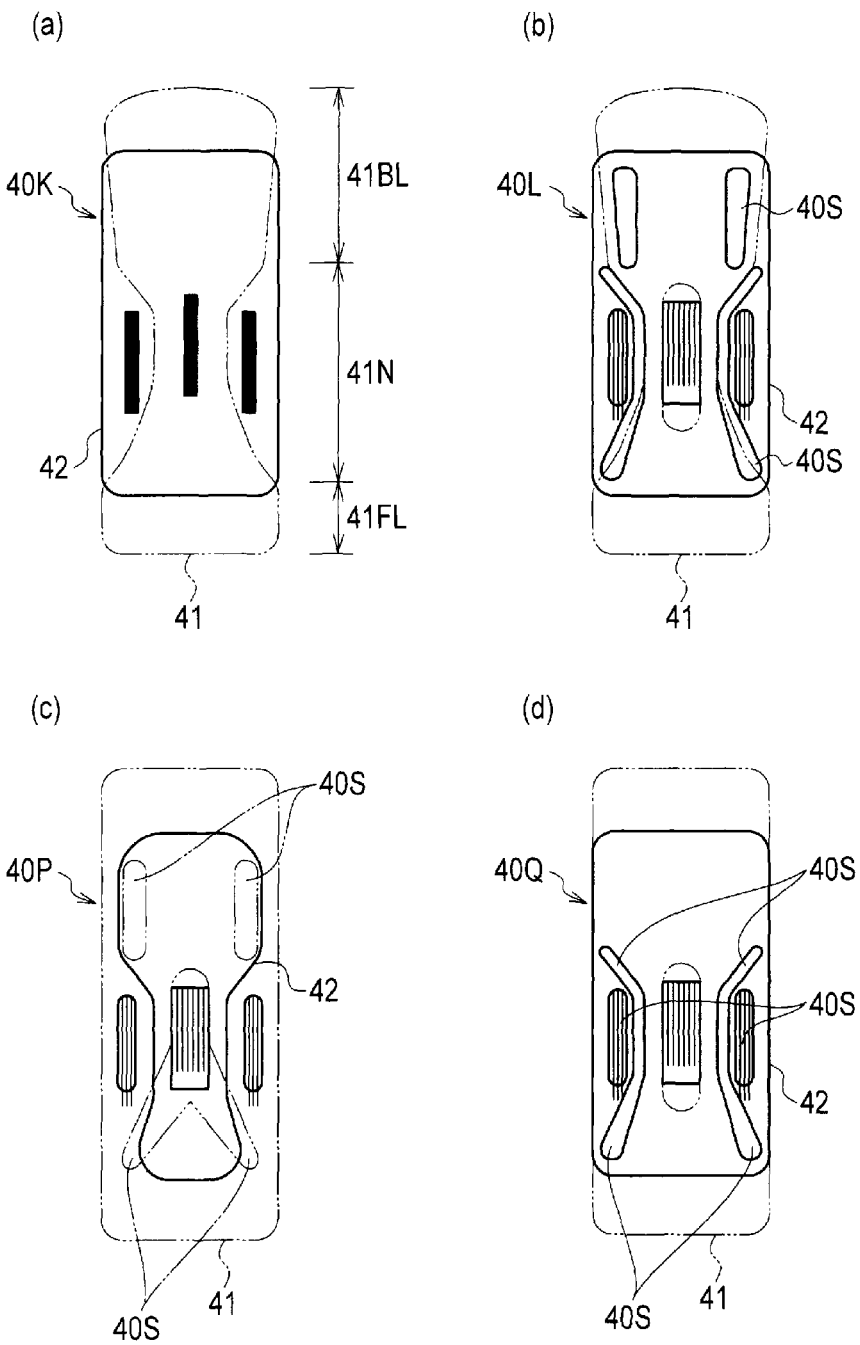
FIG. 10 is a plan view of an absorber of the disposable diaper 1 according to a third embodiment.

FIG. 10 is a plan view of the absorber of a disposable diaper according to the third embodiment. The absorber 40 according to the third embodiment is configured by a first layer 41 and a second layer 42.

The first layer of the absorber 40K shown in FIG. 10 (a) has a narrow part 41N that is concave towards the center in the widthwise direction W, and a wide part 41FL and a wide part 41BL having a width wider than the narrow part 41N. The narrow part 41N is arranged in the crotch region S1. The side ends of the narrow part 41N and the side ends of the wide part 41FL and the wide part 41BL are connected by a curve, and the first layer 41 has an hourglass-type flat shape.

A central curving unit is formed in the portion where the first layer and the second layer overlap, and first curving units are configured by the outer ends 41W of the narrow part 41N of the first layer. Furthermore, second curving units are formed in the portion where the absorber includes only the second layer 42. The second layer 42 has a rectangular shape having a lengthwise direction L and a widthwise direction W.

The first layer 41 of the absorber 40L shown in FIG. 10 (b) has an hourglass-type flat shape same as the absorber 40K shown in FIG. 10(a). A pair of slits 40S is formed both anteriorly and posteriorly with respect to the crotch region of the second layer 42. The outer end edges at the outer sides in the widthwise direction of each slit 40S almost match (i.e., substantially coincide with) the outer edges of the hourglass-type flat shape of the first layer.

In the crotch anterior portion, because the gap when the legs are closed while wearing is the least, the effect of the decline in the discomfort of the crotch of the wearer is high due to the reduction of the thickness of the absorber 40 in the crotch of the wearer. Furthermore, in the crotch posterior portion, even when the absorber 40 swells up after absorbing the bodily fluid, it is easy to maintain the gap between the absorber and the skin. Furthermore, bodily fluid such as urine, can be transferred smoothly to the first layer 41 via slits 40S.

The first layer 41 of the absorber 40P shown in FIG. 10 (c) has a rectangular shape having a lengthwise direction L and a widthwise direction W. Furthermore, the second layer 42 has an hourglass-type flat shape. A pair of slits 40S is formed both anteriorly and posteriorly with respect to the crotch region of the first layer. The outer end edges at the outer sides in the widthwise direction of each slit 40S almost match the outer edges of the second layer 42 configuring the hourglass-type flat shape.

The absorber 40Q shown in FIG. 10 (d) is configured by a first layer 41 and a second layer 42 of a rectangular shape having a lengthwise direction L and a widthwise direction W. Slits 40S positioned outboard of the central elastic member 44 configuring the central curving unit are formed in the second layer 42 to define first curving units. The slits 40S that form the first curving units further extend obliquely outwardly in both the lengthwise direction and the widthwise direction. Further slits 40S are formed outboard of the slits 40s that define the first curving units. Second curving units are formed by these further slits 40S and the first elastic members 48.

Other Embodiments

As described above, although several embodiments of the present invention are disclosed in detail, however, the description and drawings that constitute a part of this disclosure are not intended to limit the present invention. From this disclosure, various substitute embodiments, examples, and operation techniques become apparent to those ordinarily skilled in the art.

For example, in the above embodiments, the explanation is based on a pants-type disposable diaper, but the present invention is not limited thereto, and may also be applied to open-type disposable diapers, incontinence pads, and sanitary napkins.

In the above embodiments, the absorber is configured to curve by using slits, elastic members, or boundary portions with varying rigidity, however, the absorber can also be configured to curve by reducing the thickness of the absorber, and by performing embossing on the absorber.

In addition, the present invention may be described as follows.

(a) The first curving units are configured by compressed portions where the absorber is compressed in the thickness direction.

(b) The disposable wearing article may further comprising compressed portions where the absorber is compressed in the thickness direction, wherein the compressed portions are provided at both outer sides in the lengthwise direction with respect to the crotch region of the absorber, and extend obliquely outwardly in both the lengthwise direction and the widthwise direction.

(c) The disposable wearing article may further comprising a pair of third curving units formed outboard of the second curving units in the widthwise direction.

(d) The disposable wearing article may further comprising a pair of fourth curving units formed outboard of the third curving units in the widthwise direction.

(e) The disposable wearing article may further comprising slits which are provided at both outer sides in the lengthwise direction with respect to the crotch region of the absorber, and extend obliquely outwardly in both the lengthwise direction and the widthwise direction and the slits may further configure the first curving units.

(f) In the widthwise direction, the absorber has a highest rigidity between each first curving unit and the central curving unit.

Thus, it is needless to say that the present invention includes various embodiments not specifically described herein. Therefore, the technical scope of the present invention is defined only by the inventive specific matter according to the scope of the claims appropriate from the above description.

This application claims the benefit of Japanese Application No. 2011-027618 the entire disclosure of which is incorporated by reference herein.

The invention claimed is:
1. A disposable wearing article, comprising:
an absorber having a front-back direction, a widthwise direction perpendicular to the front-back direction, an inner direction for facing a wearer, and an outer direction opposite the inner direction,
wherein the absorber has a central portion formed in a center of the absorber in the widthwise direction, a pair of side end portions including side ends of the absorber in the widthwise direction, and a pair of intermediate portions positioned between the central portion and the side end portions, in a crotch region that is adapted to be in contact with a crotch of the wearer, a central curving unit that allows the absorber to curve in the inner direction in a convex shape is formed in the center of the absorber, a pair of first curving units along the front-back direction that allow the absorber to curve in the outer direction in a convex shape is formed outboard of the central curving unit of the absorber in the widthwise direction, a pair of second curving units along the front-back direction that allow the absorber to curve in the inner direction in a convex shape is formed outboard of the first curving unit of the absorber in the widthwise direction, a top surface of the absorber that takes a convex shape in the inner direction due to the central curving unit is adapted to be in contact with the crotch of the wearer, a front end of the central curving unit is positioned posteriorly of a front end of at least one of the second curving units, the absorber includes:
   a first layer positioned at a non-skin contact surface side; and
   a second layer overlapping the first layer and being positioned at a skin contact surface side, the absorber in the central portion is formed only by the second layer, the absorber positioned between the central curving unit and the first curving units is formed by the first layer and the second layer, and the absorber positioned between the first curving units and the second curving units is formed only by the second layer.

2. The disposable wearing article according to claim 1, wherein in the widthwise direction, a density of the absorber positioned between the central curving unit and the first curving units is more than a density of the absorber positioned in the central portion.

3. The disposable wearing article according to claim 1, wherein a rear end of the central curving unit is positioned posteriorly of a rear end of at least one of the second curving units.

4. The disposable wearing article according to claim 1, wherein
   the central curving unit is configured by a central elastic member arranged along the front-back direction,
   each of the second curving units is configured by a first elastic member arranged along the front-back direction, and
   in a state prior to curving of the absorber in a convex shape, the central elastic member has a stress more than that of the first elastic member.

5. The disposable wearing article according to claim 4, wherein
   the central elastic member has central portion elastic members positioned in a center of the central elastic member in the widthwise direction, and central auxiliary elastic members positioned outboard of the central portion elastic members in the widthwise direction, and
   in a state prior to curving of the absorber in a convex shape, each of the central portion elastic members has a stress more than that of each of the central auxiliary elastic members.

6. The disposable wearing article according to claim 1, wherein second elastic members are formed along the front-back direction, outboard of the second curving units of the absorber in the widthwise direction, and posteriorly of the second curving units.

7. The disposable wearing article according to claim 6, wherein the second elastic members and the second curving units do not overlap each other when seen in the widthwise direction.

8. The disposable wearing article according to claim 6, wherein
   the second elastic members and the second curving units overlap each other when seen in the widthwise direction, and
   a length of an overlapping region between the second elastic members and the second curving units in the front-back direction is below 20 mm.

9. The disposable wearing article according to claim 1, wherein the central curving unit, the first curving units, and the second curving units are configured by at least any one of outer ends provided along the front-back direction and in the widthwise direction of the first layer, slits formed in the absorber along the front-back direction, and elastic members arranged along the front-back direction.

10. A disposable wearing article, comprising:
   an absorber having a front-back direction, a widthwise direction perpendicular to the front-back direction, an inner direction for facing a wearer, and an outer direction opposite the inner direction,
wherein
   the absorber has, in a crotch region that is adapted to be in contact with a crotch of the wearer,
   a central portion formed in a center of the absorber in the widthwise direction,
   a pair of side end portions including side ends of the absorber in the widthwise direction, and
   a pair of intermediate portions positioned between the central portion and the side end portions in the widthwise direction,
   the absorber has a first layer positioned at a non-skin contact surface side and a second layer overlapping the first layer and being positioned at a skin contact surface side,
   the first layer has a length in the widthwise direction shorter than the second layer,
   a central elastic member is provided in the central portion of the absorber,
   outer ends in the widthwise direction of the first layer are arranged along the front-back direction and outboard of the central elastic member of the absorber in the widthwise direction,
   a pair of first elastic members is provided along the front-back direction and outboard of the outer ends of the first layer in the widthwise direction,
   the pair of first elastic members is provided inboard of outer ends of the second layer in the widthwise direction, and
   a front end of the central elastic member is positioned posteriorly of front ends of the first elastic members.

11. The disposable wearing article according to claim 10, further comprising a front waistline region and a back waistline region, wherein the crotch region is between the front and back waistline regions in the front-back direction, and the pair of first elastic members does not extend into the front and back waistline regions.

12. The disposable wearing article according to claim 10, wherein
a rear end of the central elastic member is positioned posteriorly of rear ends of the first elastic members.

13. The disposable wearing article according to claim 10, wherein
the central elastic member has (i) central portion elastic members and (ii) central auxiliary elastic members positioned outboard of the central portion elastic members in the widthwise direction, and
ends of the central portion elastic members and the central auxiliary elastic members are flush.

14. The disposable wearing article according to claim 10, wherein
the first layer of the absorber has a central aperture overlapping the central elastic member in a thickness direction of the absorber, and
the second layer of the absorber has a pair of slits overlapping the pair of first elastic members in the thickness direction of the absorber.

* * * * *